United States Patent [19]
Shibano et al.

[11] Patent Number: 5,952,463
[45] Date of Patent: Sep. 14, 1999

[54] PROTEINASE INHIBITOR AND GENE ENCODING THE INHIBITOR

[75] Inventors: Yuji Shibano; Norihisa Kikuchi; Kohei Oda, all of Osaka, Japan

[73] Assignee: Biomolecular Engineering Research Institute, Osaka, Japan

[21] Appl. No.: 08/878,546

[22] Filed: Jun. 19, 1997

[30] Foreign Application Priority Data

Jun. 19, 1996 [JP] Japan .................................. 8-158677
Aug. 26, 1996 [JP] Japan .................................. 8-224104
Mar. 3, 1997 [JP] Japan .................................. 9-048101

[51] Int. Cl.$^6$ .............................. A61K 38/00; C07K 1/00
[52] U.S. Cl. ........................................... 530/324; 530/350
[58] Field of Search ..................... 530/324, 350

[56] References Cited

U.S. PATENT DOCUMENTS

| | | | |
|---|---|---|---|
| 4,929,553 | 5/1990 | Bussey et al. ................. | 435/172.3 |
| 5,413,914 | 5/1995 | Franzusoff ..................... | 435/23 |
| 5,541,062 | 7/1996 | Smeekens et al. ............. | 435/6 |
| 5,627,043 | 5/1997 | Franzusoff ..................... | 435/23 |
| 5,691,183 | 11/1997 | Franzusoff et al. ............ | 435/252.3 |

OTHER PUBLICATIONS

Rudinger (Jun. 1976) Characteristics of the amino acids as components of a peptide hormone sequence. In: Peptide Hormones. Ed. J. A. Parsons. University Park Press, Baltimore, MD. pp. 1–7.

Ngo et al. (Jun. 1994) Computational complexity, protein structure prediction, and the lLevinthal paradox. In The Protein Folding Problem and Tertiary Structure Prediction. Eds. Merz et al. Birkhauser et al. Boston, MA. pp. 491–495.

Thornton et al. (Aug. 1995) Protein Engineering: Editorial Overview. Current Opinion in Biotechnology 6(4): 367–369.

Wallace (Apr. 1993) Understanding cytochrome c function: engineering protein structure by semisynthesis. The FASEB Journal 7: 505–515.

Sugino, H. et al., "Plasminostreptin, a Protein Proteinase Inhibitor Produced by *Streptomyces antifibrinolyticus*", Journal of Biological Chemistry, vol. 253, Mar. 10, 1978, pp. 1546–1555, XP002086332.

Chaudhuri, B., Stephan, C., "A C–terminal domain, which prevents secretion of the neuroendocrine protein 7b2 in *Saccharomyces cerevisiae*, inhibits Kex2 yet is processeed by the Yap3 protease" FEBS LETTER., vol. 364, 1995, pp. 91–97, XP002086333.

Seidah, N.G. et al., Mammalian Neural and Endocrine Pro–Protein and Pro–Hormone Convertases Belonging to the Subtilisin Family of Serine Proteases, Enzyme, vol. 45, 1991, pp. 271–284, XP002086334.

Angliker, H., et al., "The Synthesis of Inhibitors For Processing Proteinases and Their Action On the Kex2 Proteinase of Yeast", Biochem. J., vol. 293, 1993, pp. 75–81, XP002086335.

Oda, K., et al., "A Novel Proteinaceous Kex 2 Proteinase Inhibitor, Kexstatin, from *Streptomyces Platensis* Q268" Biosci. Biotech. Biochem., vol. 60, No. 8, 1996, pp. 1388–1389, XP002086336.

*Primary Examiner*—Robert A. Wax
*Assistant Examiner*—Einar Stole
*Attorney, Agent, or Firm*—Davidson, Davidson & Kappel, LLC

[57] ABSTRACT

The present invention relates to a novel proteinase inhibitor useful as a medicine or pesticides and a gene coding for the inhibitor. A proteinase inhibitor (Kexstatin) having inhibitory activity against Kex2 proteinase family enzymes and having a molecular weight of 11,500; a gene coding for Kexstatin; and a method for producing Kexstatin using a microorganism belonging to the genus Streptomyces or transformed with Kexstatin gene are disclosed.

11 Claims, 9 Drawing Sheets

| Lane | Restriction Enzyme |
|---|---|
| 1 | BamH I + Sal I |
| 2 | BamH I + Pst I |
| 3 | BamH I + Xho I |
| 4 | BamH I + Bgl II |
| 5 | Sal I + Pst I |
| 6 | Sal I + Xho I |
| 7 | Sal I + Bgl II |
| 8 | Pst I + Xho I |
| 9 | Pst I + Bgl II |
| 10 | Xho I + Bgl II |
| 11 | HindIII + Kpn I |
| 12 | None |

FIG. 7

```
TCGAAACCCGCCCGAACGACCGGTCGGCGGCCGGATTCATCCCCTCGGGTTCCGCCGAC      1260

CACCCCGGGCCACCTCCGGCCCGTTCGCGCCATTACTCTCAGCTTTCGGCTAATGACTCA      1320

CTTTGCCAGTGGCATGGCCGGTGCCGCATCCCCGCTGGCCGCACCCTCTTTCGCCCGGAC      1380

AAGCGATCGCCTTGTGCTCACTCAAGATGCTTTCGAGGTGCGATTGGGCCAGACTCCCGT      1440

CCGGTATCTGCACCTTCGAGC AAGGAG TGTTCGTCATGCGGTACATCACTGGGGCGGTC     1500
                             MetArgTyrIleThrGlyAlaVal                8

GCGCTCGGCGCTGCGCTGGTCCTGGGCACCCTGGCCACCACCGCACAGGCCGCCGCACCG      1560
AlaLeuGlyAlaAlaLeuValLeuGlyThrLeuAlaThrThrAlaGlnAlaAlaAlaPro         28

GCGCAGCCGGCGCGGACCGGTGGCCTCTACGCCCCGACGGAACTGGTGCTGACAGTCGGC      1620
AlaGlnProAlaArgThrGlyGlyLeuTyrAlaProThrGluLeuValLeuThrValGly         48

CAGGGCGAAAGCCGCGCGACCGCCACGGTGCAGCGTGCGGTGACGCTCAGCTGTATGCCG      1680
GlnGlyGluSerArgAlaThrAlaThrValGlnArgAlaValThrLeuSerCysMetPro         68

GGGGCCAGGGGGAGCCACCCGAACCCGCTGGGCGCCTGCACCCAACTGCGTGCGGTCGCC      1740
GlyAlaArgGlySerHisProAsnProLeuGlyAlaCysThrGlnLeuArgAlaValAla         88

GGCGACTTCAACGCGATAACCGCTGCCACCTCGGACCGGCTGTGCACCAAGGAGTGGAAC      1800
GlyAspPheAsnAlaIleThrAlaAlaThrSerAspArgLeuCysThrLysGluTrpAsn       108

CCCCTCGTGGTCACCGCCGACGGCGTGTGGCAGGGCAAGCGGGTCTCGTACAGCTACACC      1860
ProLeuValValThrAlaAspGlyValTrpGlnGlyLysArgValSerTyrSerTyrThr       128

TTCGCCAACCGCTGCGAGATGAACATCGACAGCGACACGGTCTTCAACTTCTGACCGGTC      1920
PheAlaAsnArgCysGluMetAsnIleAspSerAspThrValPheAsnPhe...             145

AGCTTGA GATCCCCGGGCACC GGAGGGT GGTGCCCGGGATC GTCCTGTGCGGGAGCAC     1980

CGGGCGAGCCGGCGCCGCCCCGGTCAGCCGATCTGCGCGCCGTAGGCCTTCAGGGCCTCG      2040

GTGACGGGCTGGAAGAAGGTCTCGCCGCCCTGGGAGCAGTCGCCGCTGCCGCCGGAGGTG      2100

AGGCCGATCGCGGCATCGCCGTCGAAGAGCGGCGCCGCTGTCGCCGGGCTCGGCCAG       2160

ACATCGGTCTGGATCAGACCGTCGAC                                        2186
```

FIG. 8

```
                 1           10          20          30          40          50          60                    70          80          90         100
                                                                                                                ♦(reactive site)
Kexstatin        GLYAPTELVL TVGQGESRAT ATVQRAVTLS CMPGARGSHP NPLGACTQLR AVAGDFNAIT --AATSDRLCT K EWNPLVVTAD GVWQGKRVSY SYTFANRCEM SCI              SLYAPSAMVF SVAQGDDVAA PTVVRATTVS CAPGARGTHP DPKAACAALK STGGAFDRLL S-EPNPDRACP M HYAPVTVSAV GVWEGRRVAW DHTFANSCTM
SIL8             SLYAPSAMVF SVAQGDDVAA PTVVRATTVS CAPGARGTHP DPKAACAALK STGGAFDRLL S-EPNPDRACP M HYAPVTVSAV GVWEGRRVAW DHTFANSCTM
PSN              GLYAPSALVL TMGHGNSAAT VNPERAVTLN CAPTASGTHP AALQACAELR GAGGDFDALT ---VRGDVACT K QFDPVVVTVD GVWQGKRVSY ERTFANECVK
SIL13            SLYAPSAIVL TMGHGESAAA VSPARAVTLN CAPSASGTHP APALACAELR AAGGDLDALA ---GPADTVCT K QYAPVVITVD GVWQGKRVSY ERTFANECVK
SIL10                YAPSALVL TVGHGESAIA ATPERAVTLT CAPKAAGTHP AAGAACAELR GVGGDFDALT ---ARDGVMCT K QYDPVVVTVE GVWQGKRVSY ERTFSNDCMK
SIL14                YAPSALVL TVGEGESAAA ATPERAVTLT CAPRPSGTHP VAGSACAELR GVGGDVHALT ---ATDGVMCT K QYDPVVVTVD GVWQGRRVSY ERTFSNECVK
SIL4        APDAAPA SLYAPSALVL TIGHGAAAT ATPERAVTLT CAPTSSGTHP AASAACAELR GVGGDFAALK ---ARDDWCN K LYDPVVVTAQ GVWQGQRVSY ERTFGNSCER
STI2             A SLYAPSALVL TVGHGTSAAA ASPLRAVTLN CAPTASGTHP APALACADLR GVGGDIDALK ---ARDGVICN K LYDPVVVTCD GVWQGKRVSY ERTFGNECVK
SIL3                 YAPSAIVL TVGHGESAAT AAPLRAVTLT CAPTASGTHP AADAACAELR AAHGDPSALA ---ADDAVMCT R EYAPVVVTVD GVWQGRRLSY ERTFANECVK
STI1             SLYAPSALVL TVGHGESAAT AAPLRAVTLT CAPTASGTHP AAAAACAELR AAHGDPSALA ---AEDSVMCT R EYAPVVVTVD GVWQGRRLSY ERTFANECVK
SIL2        TAPA SLYAPSALVL TIGQGESANA TSPLRAVTLT CAPKATGTHP AADAACAELR RAGGDFDALS ---AADGVMCT R EYAPVVVTVD GVWQGRRLSY ERTFANECVK
API                  YAPSALVL TVGKGVSAAT VTPERAVTLT CAPGPSGTHP AADSACADLA AVGGDLDALT ---RSEGVMCP M IYDPVLLTVD GVWQGERVSY ERTFVSNECEM
SSI         DAPS ALYAPSALVL TVGKGVSATT AAPERAVTLT CAPGPSGTHP AAGSACADLA AVGGDLNALT ---RGEDVMCP M VYDPVLLTVD GVWQGKRVSY ERVESNECEM
SIL1             SLYAPSAVVI SKTQGASADA PA-QRAVTLR CLP-VGGDHP APEKACAALR EAGGDPAALP RYVEDTGRVCT R EYRPVTVSVQ GVWDGRRIDH AQTFSNSCEL 110
Kexstatin        NIDSDTVFNF              Streptomyces platensis Q268

SCI              AATLDGNAVF              Streptomyces chymotrypsin inhibitor
SIL8             AATLDGNAVF              Streptomyces subtilisin inhibitor-like 8
PSN              NSYGMTVFTF              plasminostretin
SIL13            NASGSSVFAF              Streptomyces subtilisin inhibitor-like 13
SIL10            NAYGTGVESF              Streptomyces subtilisin inhibitor-like 10
SIL14            NAYGSGVFAF              Streptomyces subtilisin inhibitor-like 14
SIL4             DAVGGSLFAF              Streptomyces subtilisin inhibitor-like 4
STI2             NSYGTSLFAFI             Streptomyces trypsin inhibitor
SIL3             NAGSASVFTFA             Streptomyces subtilisin inhibitor-like 3
STI1             NAGSASVFTF              Streptomyces trypsin inhibitor
SIL2             NAGSASVFTFK             Streptomyces subtilisin inhibitor-like 2
API              NAHGSSVLAF              alkaline protease inhibitor
SSI              NAHGSSVFAF              Streptomyces subtilisin inhibitor
SIL1             EKQTASVYAFP             Streptomyces subtilisin inhibitor-like 2
```

1. Vector alone
2. Kexstatin gene inserted

SEQUENCE LISTING (1) GENERAL INFORMATION:

(iii) NUMBER OF SEQUENCES: 10

(2) INFORMATION FOR SEQ ID NO:1:

(i) SEQUENCE CHARACTERISTICS:
        (A) LENGTH: 19 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (vi) ORIGINAL SOURCE:
        (A) ORGANISM: STREPTOMYCES PLATENSIS
        (B) STRAIN: Q268

(xi) SEQUENCE DESCRIPTION: SEQ ID NO:1:

```
Gly Leu Tyr Ala Pro Thr Glu Leu Val Leu Thr Val Gly Gln Gly Glu
1               5                   10                  15

Ser Arg Ala
```

(2) INFORMATION FOR SEQ ID NO:2:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (vi) ORIGINAL SOURCE:
        (A) ORGANISM: STREPTOMYCES PLATENSIS
        (B) STRAIN: Q268

(xi) SEQUENCE DESCRIPTION: SEQ ID NO:2:

```
Ala Thr Ala Thr Val Gln Arg
1               5
```

(2) INFORMATION FOR SEQ ID NO:3:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (vi) ORIGINAL SOURCE:
        (A) ORGANISM: STREPTOMYCES PLATENSIS
        (B) STRAIN: Q268

(xi) SEQUENCE DESCRIPTION: SEQ ID NO:3:

```
Gly Ser His Pro Asn Pro Leu Gly Ala Cys Thr Gln Leu Arg
1               5                   10
```

(2) INFORMATION FOR SEQ ID NO:4:

(i) SEQUENCE CHARACTERISTICS:
        (A) LENGTH: 11 amino acids
        (B) TYPE: amino acid -continued (C) STRANDEDNESS: single
         (D) TOPOLOGY: linear (ii) MOLECULE TYPE: protein (iii) HYPOTHETICAL: NO (iv) ANTI-SENSE: NO (vi) ORIGINAL SOURCE:
         (A) ORGANISM: STREPTOMYCES PLATENSIS
         (B) STRAIN: Q268

(xi) SEQUENCE DESCRIPTION: SEQ ID NO:4:

Ala Val Thr Leu Ser Cys Met Pro Gly Ala Arg
1               5                   10

(2) INFORMATION FOR SEQ ID NO:5:

(i) SEQUENCE CHARACTERISTICS:
         (A) LENGTH: 18 amino acids
         (B) TYPE: amino acid
         (C) STRANDEDNESS: single
         (D) TOPOLOGY: linear (ii) MOLECULE TYPE: protein (iii) HYPOTHETICAL: NO (iv) ANTI-SENSE: NO (vi) ORIGINAL SOURCE:
         (A) ORGANISM: STREPTOMYCES PLATENSIS
         (B) STRAIN: Q268

(xi) SEQUENCE DESCRIPTION: SEQ ID NO:5:

Gly Leu Tyr Ala Pro Thr Glu Leu Val Leu Thr Val Gly Gln Gly Glu
1               5                   10                  15

Ser Arg (2) INFORMATION FOR SEQ ID NO:6:

(i) SEQUENCE CHARACTERISTICS:
         (A) LENGTH: 17 amino acids
         (B) TYPE: amino acid
         (C) STRANDEDNESS: single
         (D) TOPOLOGY: linear (ii) MOLECULE TYPE: protein (iii) HYPOTHETICAL: NO (iv) ANTI-SENSE: NO (vi) ORIGINAL SOURCE:
         (A) ORGANISM: STREPTOMYCES PLATENSIS
         (B) STRAIN: Q268

(xi) SEQUENCE DESCRIPTION: SEQ ID NO:6:

Glu Trp Asn Pro Leu Val Val Thr Ala Asp Gly Val Trp Gln Gly Lys
1               5                   10                  15

Arg (2) INFORMATION FOR SEQ ID NO:7:

(i) SEQUENCE CHARACTERISTICS:
         (A) LENGTH: 249 base pairs
         (B) TYPE: nucleic acid
         (C) STRANDEDNESS: double
         (D) TOPOLOGY: linear (ii) MOLECULE TYPE: DNA (genomic)

-continued (iii) HYPOTHETICAL: NO (iv) ANTI-SENSE: NO (vi) ORIGINAL SOURCE:
         (A) ORGANISM: STREPTOMYCES PLATENSIS
         (B) STRAIN: Q268

(ix) FEATURE:
         (A) NAME/KEY: CDS
         (B) LOCATION: 1..249

(xi) SEQUENCE DESCRIPTION: SEQ ID NO:7:

```
TAC GCG CCG ACG GAA CTG GTG CTG ACA GTC GGC CAG GGC GAA AGC CGC      48
Tyr Ala Pro Thr Glu Leu Val Leu Thr Val Gly Gln Gly Glu Ser Arg
 1               5                  10                  15

GCG ACC GCC ACG GTG CAG CGT GCG GTG ACG CTC AGC TGT ATG CCG GGG      96
Ala Thr Ala Thr Val Gln Arg Ala Val Thr Leu Ser Cys Met Pro Gly
             20                  25                  30

GCC AGG GGG AGC CAC CCG AAC CCG CTG GGC GCC TGC ACC CAA CTG CGT     144
Ala Arg Gly Ser His Pro Asn Pro Leu Gly Ala Cys Thr Gln Leu Arg
         35                  40                  45

GCG GTC GCC GGC GAC TTC AAC GCG ATA ACC GCT GCC ACC TCG GAC CGG     192
Ala Val Ala Gly Asp Phe Asn Ala Ile Thr Ala Ala Thr Ser Asp Arg
     50                  55                  60

CTG TGC ACC AAG GAG TGG AAC CCC CTC GTG GTC ACC GCC GAC GGC GTC     240
Leu Cys Thr Lys Glu Trp Asn Pro Leu Val Val Thr Ala Asp Gly Val
 65                  70                  75                  80

TGG CAG GGC                                                          249
Trp Gln Gly
```

(2) INFORMATION FOR SEQ ID NO:8:

(i) SEQUENCE CHARACTERISTICS:
        (A) LENGTH: 83 amino acids
        (B) TYPE: amino acid
        (D) TOPOLOGY: linear (ii) MOLECULE TYPE: protein (xi) SEQUENCE DESCRIPTION: SEQ ID NO:8:

```
Tyr Ala Pro Thr Glu Leu Val Leu Thr Val Gly Gln Gly Glu Ser Arg
 1               5                  10                  15

Ala Thr Ala Thr Val Gln Arg Ala Val Thr Leu Ser Cys Met Pro Gly
             20                  25                  30

Ala Arg Gly Ser His Pro Asn Pro Leu Gly Ala Cys Thr Gln Leu Arg
         35                  40                  45

Ala Val Ala Gly Asp Phe Asn Ala Ile Thr Ala Ala Thr Ser Asp Arg
     50                  55                  60

Leu Cys Thr Lys Glu Trp Asn Pro Leu Val Val Thr Ala Asp Gly Val
 65                  70                  75                  80

Trp Gln Gly
```

(2) INFORMATION FOR SEQ ID NO:9:

(i) SEQUENCE CHARACTERISTICS:
        (A) LENGTH: 2186 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
(A) ORGANISM: STREPTOMYCES PLATENSIS
(B) STRAIN: Q268

(ix) FEATURE:
(A) NAME/KEY: CDS
(B) LOCATION: 1477..1911

(xi) SEQUENCE DESCRIPTION: SEQ ID NO:9:

```
GGATCCGGTG GGTGGTCGCC CGGCCGATGC CCGAGCCCGC TCCGGTGATC AGGGTGCGGC      60

GGCCGTCAAA GCGGTTCATG GTCCAGCTCC GTTCTCGAGG TACTCGCGCA CGGTATGCCG     120

ACCTGGCACA GTGTGCCAAT TACGCATGGC GTGCCGGAAT CGGCAGGACC CTCCGTAAGC     180

TGGCGCCATG CCCACCGCCC CCCGCCCCGC CGCACTCCCC CGCCCCTCGC TCACCGAGCG     240

GCGCAAGGCC GAGACCCAGC TGGAGATCGC CCGTACCGCG GCGGCCCTGT TCACGGAGCG     300

CGGCCCCGCC GTCACCGCCG AGGAGATCGC CCGTGCCGCC GGGGTCGCGC TGCGCACCTT     360

CTACCGCTAC TTCCGCACCA AGGAGGACGC GGTGGTCCCG CTGCTCGCCG ACGGGGTGCG     420

GCAGTGGATC GACGACCTGG CCGCCCCCGC ACCCGGCCCG GACGCGCCCT CCGTGCGCGA     480

GGTGCTGGAG CGGACGGCCC GCCGGTCGCT GACCCCCGCC GACGACCGGC CGCCGAGCAC     540

TGCGCTGGAC CCGTGGGCTG CTGCGGGCGA TGCCGGGCGA TCCCGCGCTG CGTGCGGTGT     600

GGCACCGGTG CACCACGACG CCGAGAGCGC TGGTGCCGGC CCTGGCACGG CTGACCGGCG     660

CACCGCCGCT GGAGGTGCGG CTGGCCGCGG CCGCCGCGAA CACCGCGATG CGGATCGCGG     720

TGGAGGAGTG GGCGGCGGGC GACGAGGCGC CGGACGACGG ACCGGAGGGG CCCGGCGCAC     780

TGGCGGCCCG GTGCCTGCGG GCGCTGACGG CCGGGCTGCC CCAGTTGGAC GGGGCGGCGG     840

AGGCCGGGCC CGGGCCCGGG CCCGGGTGAC GGCCGGCGGC TCCGGGGCCC GCGCGGCGGC     900

CGGACCCCGT GCTCATGCGG CGGTCGAATC CGGCGGGGGC CGCGGCCCGT ACGCACGACG     960

CCCCCGCGCG ACGACCGATT CCGGCTCACG CCCGGCGGCC GGCCCCGGCA CTGACACAAC    1020

GACCGCCCCC GGGCCCTTCC GCCCGTACCC GTAACGCCCC CACATCGCCG CCGACTTCGC    1080

GACGGCAAAG CAAGAAACAG GCGACGGTAA GGCGAGCAGC AGGTGGCCGG TTCTTACCGC    1140

GTCGGGCGCT CCGGGCAGCA CGGAGGGGCC TCCGCCCTCT CTTCAGCCAA TCGACGGAGA    1200

TCGAAACCCG CCCGAACGAC CGGTCGGCGG CCGGATTCAT CCCCTCCGGG TTCCGGCGAC    1260

CTTTGCCAGT GGCATGGCCG GTGCCGCATC CCCGCTGGCC GCACCCTCTT TCGCCCGGAC    1320

CACCCCGGGC CACCTCCGGC CCGTTCGCGC CATTACTCTC AGCTTTCGGC TAATGACTCA    1380

AAGCGATCGC CTTGTGCTCA CTCAAGATGC TTTCGAGGTG CGATTGGGCC AGACTCCCGT    1440

CCGGTATCTG CACCTTCGAG CAAGGGAGTG TTCGTC ATG CGG TAC ATC ACT GGG     1494
                                        Met Arg Tyr Ile Thr Gly
                                         1               5

GCG GTC GCG CTC GGC GCT GCG CTG GTC CTG GGC ACC CTG GCC ACC ACC     1542
Ala Val Ala Leu Gly Ala Ala Leu Val Leu Gly Thr Leu Ala Thr Thr
            10                  15                  20

GCA CAG GCC GCC GCA CCG GCG CAG CCG GCG CGG ACC GGT GGC CTC TAC     1590
Ala Gln Ala Ala Ala Pro Ala Gln Pro Ala Arg Thr Gly Gly Leu Tyr
        25                  30                  35

GCC CCG ACG GAA CTG GTG CTG ACA GTC GGC CAG GGC GAA AGC CGC GCG     1638
Ala Pro Thr Glu Leu Val Leu Thr Val Gly Gln Gly Glu Ser Arg Ala
    40                  45                  50

ACC GCC ACG GTG CAG CGT GCG GTG ACG CTC AGC TGT ATG CCG GGG GCC     1686
Thr Ala Thr Val Gln Arg Ala Val Thr Leu Ser Cys Met Pro Gly Ala
55                  60                  65                  70
```

```
AGG GGG AGC CAC CCG AAC CCG CTG GGC GCC TGC ACC CAA CTG CGT GCG      1734
Arg Gly Ser His Pro Asn Pro Leu Gly Ala Cys Thr Gln Leu Arg Ala
                75                  80                  85

GTC GCC GGC GAC TTC AAC GCG ATA ACC GCT GCC ACC TCG GAC CGG CTG      1782
Val Ala Gly Asp Phe Asn Ala Ile Thr Ala Ala Thr Ser Asp Arg Leu
                90                  95                 100

TGC ACC AAG GAG TGG AAC CCC CTC GTG GTC ACC GCC GAC GGC GTG TGG      1830
Cys Thr Lys Glu Trp Asn Pro Leu Val Val Thr Ala Asp Gly Val Trp
               105                 110                 115

CAG GGC AAG CGG GTC TCG TAC AGC TAC ACC TTC GCC AAC CGC TGC GAG      1878
Gln Gly Lys Arg Val Ser Tyr Ser Tyr Thr Phe Ala Asn Arg Cys Glu
               120                 125                 130

ATG AAC ATC GAC AGC GAC ACG GTC TTC AAC TTC TGACCGGTCA GCTTGAGATC    1931
Met Asn Ile Asp Ser Asp Thr Val Phe Asn Phe
135                 140                 145

CCCGGGCACC GGAGGGTGGT GCCCGGGGAT CGTCCTGTGC GGGGAGCACC GGGCGAGCCG    1991

GCGCCGCCCC GGTCAGCCGA TCTGCGCGCC GTAGGCCTTC AGGGCCTCGG TGACGGGCTG    2051

GAAGAAGGTC TCGCCGCCCT GGGAGCAGTC GCCGCTGCCG CCGGAGGTGA GGCCGATCGC    2111

GGCATCGCCG TCGAAGAGCG CGCCGCCGCT GTCGCCGGGC TCGGCGCAGA CATCGGTCTG    2171

GATCAGACCG TCGAC                                                    2186
```

(2) INFORMATION FOR SEQ ID NO:10:

(i) SEQUENCE CHARACTERISTICS:
       (A) LENGTH: 110 amino acids
       (B) TYPE: amino acid
       (C) STRANDEDNESS: single
       (D) TOPOLOGY: linear (ii) MOLECULE TYPE: protein (iii) HYPOTHETICAL: NO (iv) ANTI-SENSE: NO (vi) ORIGINAL SOURCE:
       (A) ORGANISM: STREPTOMYCES PLATENSIS
       (B) STRAIN: Q268

(xi) SEQUENCE DESCRIPTION: SEQ ID NO:10:

```
Gly Leu Tyr Ala Pro Thr Glu Leu Val Leu Thr Val Gly Gln Gly Glu
1               5                  10                  15

Ser Arg Ala Thr Ala Thr Val Gln Arg Ala Val Thr Leu Ser Cys Met
                20                  25                  30

Pro Gly Ala Arg Gly Ser His Pro Asn Pro Leu Gly Ala Cys Thr Gln
                35                  40                  45

Leu Arg Ala Val Ala Gly Asp Phe Asn Ala Ile Thr Ala Ala Thr Ser
     50                  55                  60

Asp Arg Leu Cys Thr Lys Glu Trp Asn Pro Leu Val Val Thr Ala Asp
65                  70                  75                  80

Gly Val Trp Gln Gly Lys Arg Val Ser Tyr Ser Tyr Thr Phe Ala Asn
                85                  90                  95

Arg Cys Glu Met Asn Ile Asp Ser Asp Thr Val Phe Asn Phe
                100                 105                 110
```

PROTEINASE INHIBITOR AND GENE ENCODING THE INHIBITOR

BACKGROUND OF THE INVENTION

1. Field of the Invention

The present invention relates to a novel proteinase inhibitor having inhibitory activity against Kex2 proteinase family enzymes, a method for producing the proteinase inhibitor, and a gene encoding the inhibitor.

2. Prior Art

Physiologically active peptides and enzyme proteins are produced as an inactive precursor and then processed into an active, mature peptide or protein through processing by a specific proteinase in many cases. At the site of such processing, a paired basic amino acids such as arginine or lysine are found. Kex2 proteinase derived from the yeast Saccharomyces is the first proteinase which has been found as a specific proteinase recognizing this paired basic amino acids in a substrate and cleaving the substrate on the carboxyl terminal side of the pair. Kex2 proteinase is a serine proteinase involved in the processing of a mating factor of yeast. The carboxyl terminal of Kex2 proteinase is penetrating into the Golgi membrane of yeast and this proteinase performs the processing of the α-factor precursor and killer toxin precursor coming into Golgi bodies to thereby allow them to be secreted as an active from α-factor and killer toxin.

A large number of serine proteinases having a structure and a specificity similar to those of Kex2 proteinase have also been found in mammals. It has been made clear that they play an important role in the processing of precursor proteins as a Kex2 proteinase family enzyme (Seidah, N. G., et al. (1991) Enzyme, 45: 271–284). Furin, PACE4 and PC5/6 are Kex2 proteinase family enzymes found in almost every tissue and involved in the processing of precursor proteins of growth factors, serum proteinases, receptors, glycosylated viral coat proteins, exotoxins from *Pseudomonal aeruginosa,* etc. Proteinases such as PC1/3, PC2, PC4 are expressed cell- or tissue-specifically and mainly involved in the processing of neuropeptides and peptide hormones (Hook, V. Y. H. et al., (1994) FASEB J., 8: 1269–1278).

Recently, there have been increased demands for highly safe and yet highly effective medicines and pesticides. Under the circumstances, researches on physiologically active peptides and proteins derived from microorganism and on the utilization of a portion of their structures as a medicine or pesticides have been positively made. Among all, compounds those which inhibit the activities of enzymes functioning at various phases of biological functions, i.e., enzyme inhibitors are used widely as medicines and pesticides. It can be said that most of medicines and pesticides are enzyme inhibitors. With respect to proteinase inhibitors also, a large number of novel peptides and proteins have been found as proteinase inhibitors as a result of search for substances inhibiting various proteinase activities. Further, these proteinase inhibitors per se or portions of their structures have been synthesized and developed as medicines and pesticides.

OBJECTS AND SUMMARY OF THE INVENTION

As described above, Kex2 proteinase family enzymes are playing the important role of processing/activating various physiologically active peptides and enzymes in organisms. If an inhibitor against Kex2 proteinase family enzymes has been found, the inhibitor per se or a compound having a structure involved in its inhibitory activity can control the processing/activation of neuropeptides and peptide hormones. Thus, such an inhibitor or compound is expected to have applications as medicines or pesticides. It is an object of the present invention to provide an inhibitor against Kex2 proteinase family enzymes, a method for producing the inhibitor and a gene coding for the inhibitor.

In view of the important role of Kex2 proteinase family enzymes in biological systems, the present inventors have screened a wide range of microorganism cultures to find out a substance inhibiting yeast Kex2 proteinase activity. As a result, it has been found that a strain belonging to the genus Streptomyces produces and accumulates in the culture fluid a substance having an activity strongly inhibiting the activity of the yeast Kex2 proteinase. Thus, the present invention has been achieved.

The present invention relates to a proteinase inhibitor having inhibitory activity against Kex2 proteinase family enzymes and having a molecular weight of 11,500, and a method for producing the inhibitor using a microorganism.

The present invention also relates to a gene coding for a protein having the amino acid sequence shown in SEQ ID NO:10 or a protein which has the amino acid sequence shown in SEQ ID NO:10 having deletion, replacement or addition of one or several amino acid residues and which has inhibitory activity against Kex2 proteinase family enzymes.

BRIEF DESCRIPTION OF THE DRAWINGS

FIG. 7 shows the nucleotide sequence for a DNA fragment containing a Kexstatin gene and the deduced amino acid sequence for Kexstatin.

FIG. 8 shows the amino acid sequences for Kexstatin and various proteinase inhibitors belonging to the SSI family.

DETAILED DESCRIPTION OF THE INVENTION

Figure 1:
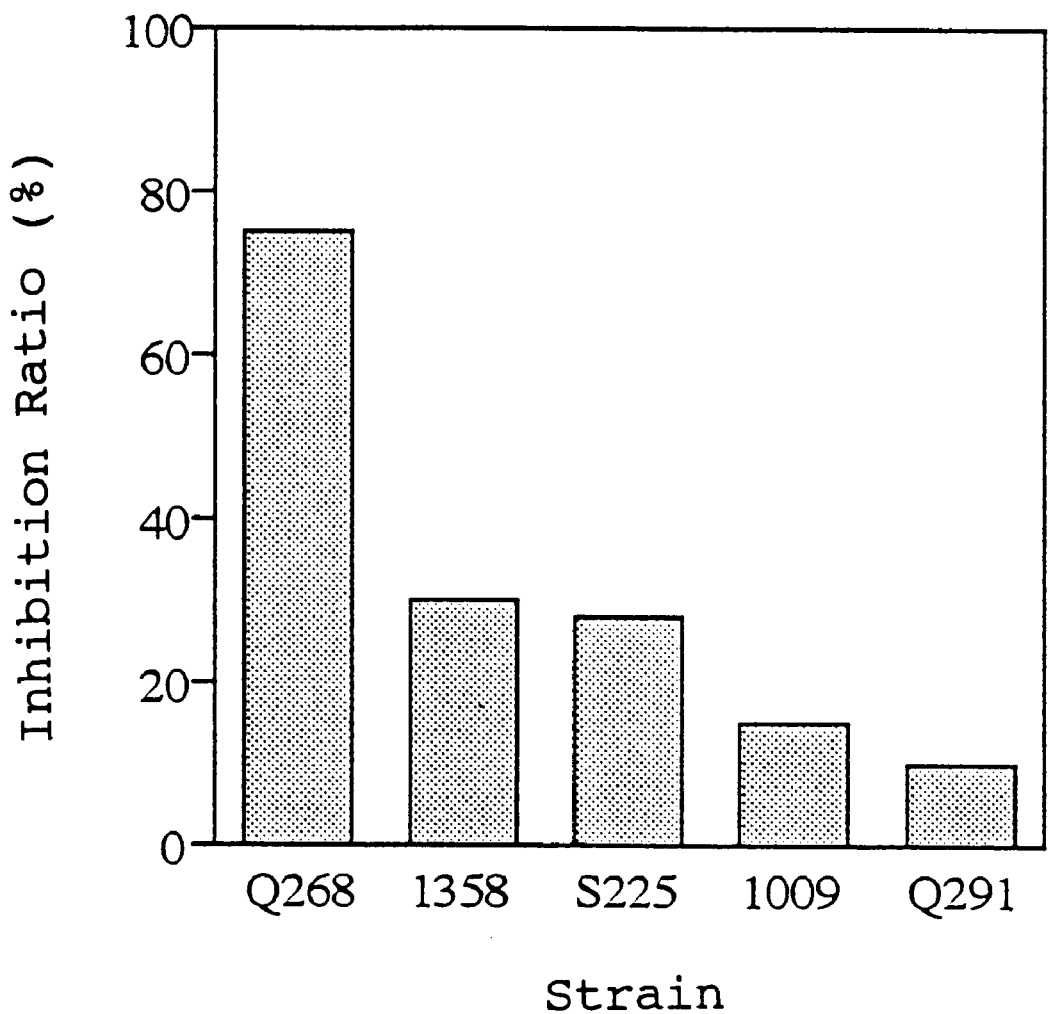
FIG. 1 is a graph showing the inhibition ratio of the inhibitor isolated against Kex2 proteinase.

Hereinbelow, the present invention will be described in detail.

(1) Proteinase Inhibitor (Kexstatin)

The proteinase inhibitor of the present invention has the following properties.

i) Target Enzymes

The proteinase inhibitor of the invention has remarkable inhibitory activity against Kex2 proteinase family enzymes and subtilisin. It also inhibits trypsin, but does not inhibit chymotrypsin and thermolysin. The term "Kex2 proteinase family enzymes" means a group of specific proteinases which, similar to Kex2 proteinase, recognize -Lys-Arg- or -Arg-Arg- in a substrate and cleave the substrate at the carboxyl terminal side of the paired basic amino acid.

ii) Molecular Weight

The molecular weight of the proteinase inhibitor of the invention is 11,500 as determined by SDS-polyacrylamide gel electrophoresis.

iii) Amino Acid Sequence

The proteinase inhibitor of the invention has an amino acid sequence comprising the amino acid sequence shown in SEQ ID NO: 10 or the amino acid sequence shown in SEQ ID NO: 10 having deletion, substitution or addition of one or more amino acid residues. The "deletion, substitution or addition" can be generated by conventional techniques at the time of the filing of the present application, such as site-specific mutagenesis (Nucleic Acid Research, vol. 10, No. 20, pp. 6487–6500).

iv) Thermostability

The inhibitory activity of the proteinase inhibitor of the invention is not lost even after two times of a heat treatment at 100° C. for 5 minutes.

v) pH Stability

The proteinase inhibitor is stable at pH 6–8.

The above-described properties of the proteinase inhibitor of the invention were compared with those of known proteinase inhibitors. As a result, the N-terminal amino acid sequence and partial amino acid sequences have shown a high similarity to those of Streptomyces subtilisin inhibitor (SSI) which is an inhibitor against subtilisin. However, the proteinase inhibitor of the invention is clearly different from SSI in one point that SSI does not inhibit Kex2 proteinase. Thus, the proteinase inhibitor of the invention has been recognized as a novel substance. This substance has been designated "Kexstatin" since it inhibits the Kex2 proteinase activity.

As described earlier, enzyme inhibitors are widely used in medicines and pesticides and Kexstatin is also applicable as a medicine or pesticides. Specifically, Kexstatin can be used for treating hormone secretion abnormalities, viral infections, etc. since it inhibits the production of peptide hormones and glycosylated viral coat sugar proteins.

Kexstatin can be produced by culturing a strain of microorganism in a medium and recovering Kexstatin from the culture.

The microorganism used for this purpose is not particularly limited as long as it belongs to the genus Streptomyces and has a Kexstatin-producing ability. As a preferable strain, the strain Q268 may be given. Q268 is a strain which has been isolated from a soil in Sendai City, Miyagi Pref., Japan. The bacteriological properties of this strain are as follows.

[Bacteriological Properties of Q268]

This strain is one of the actinomycetes which was newly isolated in October, 1995 from a soil sample taken in Sendai City, Miyagi Pref., Japan. The results of taxonomic examination of this strain are described below.

i) Morphological Characters

The subject strain shows good growth on yeast/malt agar medium, oatmeal agar medium, starch/inorganic salt medium, glycerol/asparagine agar medium, etc. On these media, this strain forms aerial hyphae abundantly and reveals good adhesion of spores. Hyphae to which spores adhered adhere on an aerial hypha, simply branching from the main axis of the aerial hypha to form lateral branches. The end of a spore-adhered hypha is spiral. The spore chain is relatively long. The number of spores per one chain is 20 to 30. As a result of observation with an electron microscope, it has been found that most of spores have a long cylindrical shape 0.5–0.7 μm wide and 0.7–0.9 μm long. Sometimes, spores of a semicircular shape have also been observed. The surface of the spores is smooth. There has not been observed any sporangium, flagellar spore nor sclerotium.

ii) Various Properties on Culturing (at 28° C. for 14 days)

The following designations of colors are based on "Color Standards" published by Nippon Shikisai Kenkyujo.

TABLE 1

| Medium | Growth | Aerial Hypha Formation | Color | Substrate Hypha | Soluble Pigment |
|---|---|---|---|---|---|
| Yeast/malt agar medium | Good | Good | Bright brown gray (Gy)* | Yellow brown | Yellow brown |
| Oatmeal agar medium | Good | Good | Brown gray (Gy)* | Light yellow brown | — |
| Starch/inorganic salt agar medium | Good | Good | Bright brown gray (Gy)* | Light yellow brown | Light brown |
| Glycerol/asparagine agar medium | Good | Good | Bright brown gray (Gy)* | Light yellow brown | — |

The media used in this experiment were those manufactured by DIFCO.
*: (Gy) represents the gray color series in ISP color series.

On all of the four media used above, the surface of colonies became wet and black as time passed, presenting the so-called "hygroscopic" state.

Growth temperature:

The strain grows at 14–35° C. The optimum growth temperature is 24–28° C.

iii) Physiological Properties

Melanoid pigment producing ability: negative

Tyrosinase reaction: negative

Starch hydrolyzing ability: positive iv) Sugar Utilizing Ability (−:negative; +:positive; ++;strongly positive)

L-Arabinose: −

D-Xylose: +

D-Glucose: ++

D-Fructose: ++

Sucrose: ++

Inositol: ++

L-Rhamnose: −

Raffinose: ++

D-Mannitol: ++ v) Composition of the Cell Wall

As a result of analysis of diaminopimelic acid which is a cell wall component, the cell wall type was found to be LL-type.

From the properties described above, the subject strain can be judged as a strain belonging to the genus Streptomyces. As a result of search for species closely related to the subject strain from Waksman, The Actinomycetes, vol.2 (1961); Shirling and Gottlieb, International Streptomyces Project Report in International Journal of Systematic Bacteriology, vol. 18, pp. 69–189 and 279–392 (1986), vol. 19, pp. 391–512 (1969) and vol. 22, pp. 265–394 (1972); Bergey's Manual of Determinative Bacteriology, 8th ed. (1974); and Bergey's Manual of Systematic Bacteriology, vol. 4, 4th ed. (1989), the subject strain was fairly identical with *Stpreptomyces platensis*, Pittenger and Gottlieb in major properties. Thus, the subject strain has been identified as a strain of *Stpreptomyces platensis* and designated *Stpreptomyces platensis* Q268.

This strain was deposited at the National Institute of Bioscience and Human-technology, Agency of Industrial Science and Technology (3 Higashi 1-chome, Tsukuba City, Ibaragi Pref., Japan) under the accession number FERM BP-5966 on May 22, 1996.

In the culturing of the microorganism used in the present invention, conventional methods for culturing microorganisms belonging to the genus Streptomyces in general are applicable. As a medium, any medium may be used as long as it contains assimilable carbon sources and nitrogen sources appropriately. As carbon sources, glucose, fructose and the like may be used. As nitrogen sources, ammonium sulfate, asparagine and the like may be used. For the growth promotion of the microorganism or the promotion of Kexstatin production, a soluble starch or the like may be added to the medium. Specific media which can be used in the invention include Waksman medium and starch/inorganic salt medium. It is preferable to maintain the pH of the medium at 7.0–7.2. Also, it is preferable to maintain the temperature during cultivation at 24–28° C. When the cultivation has been continued for a long period, the inhibitory activity of Kexstatin may be reduced. Thus, it is desirable to stop the cultivation when the microorganism has grown to a certain degree. Specifically, it is preferable to make the cultivation period 24–72 hours.

Kexstatin can be obtained not only from a natural microorganism as described above. It is also possible to obtain Kexstatin by introducing Kexstatin gene described below to a host cell (preferably, a microorganism cell), culturing the resultant transformant and recovering Kexstatin from the culture. As a host microorganism, prokaryotic cells such as *E. coli* and actinomycetes and eukaryotic cells such as yeast may be used. In *E. coli* and yeast, vectors for introducing Kexstatin gene have been known and promoters necessary for expressing Kexstatin gene have also been known. As a transformation/expression system in actinomycetes, a system in which the host is *Streptomyces libidans* (Katoh, K. et al., (1995), J. Ferment. Bioeng., 80: 440–445) is known.

The recovery of Kexstatin from the culture can be performed by conventional methods for recovering a protein from a culture fluid of microorganism. For example, a culture fluid is obtained by removing cells by centrifugation or the like. Then, this supernatant is purified by ammonium sulfate fractionation, gel filtration and the like to thereby isolate Kexstatin.

(2) Kexstatin Gene

Kexstatin gene of the present invention codes for a protein having an amino acid sequence comprising the amino acid sequence shown in SEQ ID NO: 8 or SEQ ID NO:10 or a protein which as amino acid sequence comprising the amino acid sequence shown in SEQ ID NO: 8 or SEQ ID NO:10 having deletion, substitution or addition of one or several amino acid residues and which has inhibitory activity against Kex2 proteinase family enzymes. As described earlier, the "deletion, substitution or addition" can be generated by conventional techniques at the time of the filing of the present application, such as site-specific mutagenesis (Nucleic Acid Research, vol. 10, No. 20, pp. 6487–6500).

Kexstatin gene can be obtained as follows.

First, PCR primers are designed based on the partial amino acid sequence for Kexstatin described below. A PCR is performed using these primers and the genomic DNA of *Streptomyces platensis* as a template. The amino acid sequence deduced from the nucleotide sequence for the resultant PCR product is confirmed to be consistent with the partial amino acid sequences based on which the primers have been designed. The genomic DNA of *Streptomyces platensis* is completely digested with various restriction enzymes and fractionated by agarose gel electrophoresis. Using the PCR product as a probe, Southern hybridization is performed to find restriction enzymes which generate the minimum DNA fragment containing the entire region of Kexstatin gene. Using the genomic DNA of *Streptomyces platensis* completely digested with these restriction enzymes, a genomic library is prepared. Then, a clone having Kexstatin gene is selected by colony hybridization using the PCR product described above as a probe. Plasmids are extracted from the positive clone and it is confirmed that they comprise the sequence of the PCR product described above by Southern hybridization analysis. Also, the nucleotide sequence for the inserted fragment is determined and then it is confirmed that the amino acid sequence deduced therefrom is consistent with the partial amino acid sequence of Kexstatin described below.

Alternatively, since the nucleotide sequence for Kexstatin gene has been already shown in SEQ ID NO:9, Kexstatin gene can also be obtained by synthesizing a sense primer and an antisense primer corresponding to the 5' end and 3' end of the DNA represented by SEQ ID NO:9, respectively, and performing a PCR using the genomic DNA of *Streptomyces platensis* as a template.

PREFERRED EMBODIMENTS OF THE INVENTION

Hereinbelow, the present invention will be described in more detail with reference to the following Examples.

EXAMPLE 1

Search for a Substance Inhibiting Kex2 Proteinase Activity

Although Kex2 proteinase is a membrane-bound enzyme, this enzyme can be secreted into a medium by creating KEX2 gene (sKEX2) having deletion of the transmembrane portion at the carboxyl terminal and expressing the gene in Saccharomyces yeast (Gluschankof, P. & Fuller, R. S. (1994) EMBO J., 13: 2280–2288). The Saccharomyces yeast transformed with sKEX2 gene was cultured. The Kex2 proteinase in the culture solution was subjected to ammonium sulfate fractionation and then purified to electrophoretic homogeneity by chromatography using Q Sepharose, Phenyl Superose and Superdex 75.

The assay of inhibitory activity against Kex2 proteinase was performed as follows. Briefly, to 10 $\mu$l of the purified secretion-type Kex2 proteinase (100 $\mu$g/ml), 10 $\mu$l of a microorganism culture broth heat-treated at 100° C. for 5 min and 50 $\mu$l of 0.125 mM synthetic fluorescent substrate [Boc-Gln-Arg-Arg-MCA (Boc: t-butoxycarbonyl; MCA: methylcoumarinamide)] were added and incubated at 37° C. for 10 min. The reaction was terminated by adding 940 $\mu$l of 0.125 M zinc sulfate and the fluorescence intensity was measured using an excitation wave length of 385 nm and a fluorescence wave length of 465 nm. Inhibition ratio (%) was obtained by subtracting (a) fluorescence intensity when the culture solution was added from (b) fluorescence intensity when no culture solution was added, dividing the difference by (b) and multiplying the resultant value by 100. The amount of inhibiting substance which gives 50% inhibition ratio was regarded as 1 IU (inhibitor unit).

The present inventors examined culture solutions of about 1700 strains of actinomycetes isolated from various soils throughout Japan. As a result, inhibitory activity against Kex2 proteinase was recognized in culture fluid of 5 strains.

The inhibition ratios of these culture fluid are shown in FIG. 1. As seen from this Figure, the culture fluid of Q268 strain exhibited the highest inhibition ratio. Thus, it was decided to purify the inhibiting substance from Q268 strain.

EXAMPLE 2

Examination of the Properties of the Inhibiting Substance in the Culture Fluid of Q268 Strain Q268 strain was cultured in 6 ml of Waksman medium [0.1% glucose, 0.5% polypeptone, 0.5% meat extract, 0.3% NaCl (pH 7.0)] for 2 days. Then, about 2 ml of the culture was inoculated into a Sakaguchi flask containing 100 ml of Waksman medium. After 24 hr of cultivation, cells were removed by centrifugation and the resulting culture fluid was treated at 100° C. for 5 min, to thereby obtain a sample.

Figure 2:
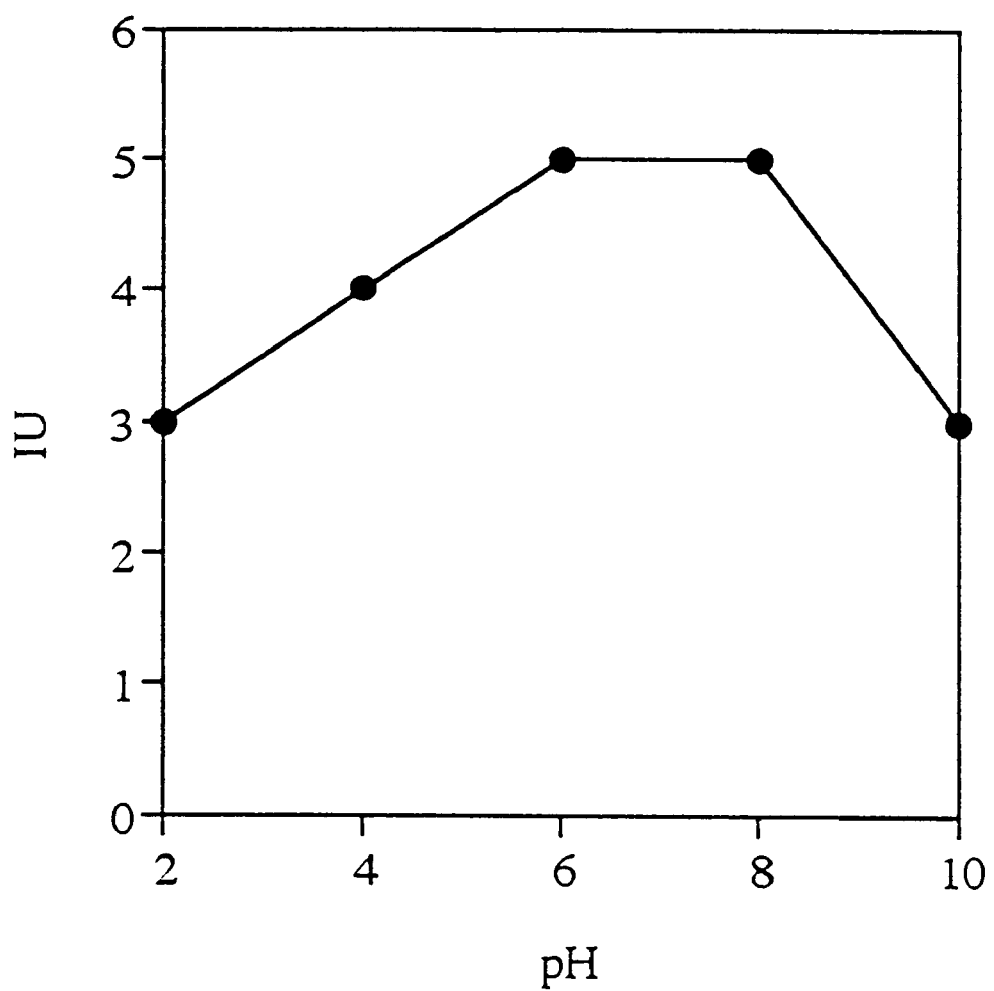
FIG. 2 is a graph showing the pH stability of Kexstatin.

The above sample was again treated at 100° C. for 5 min but the inhibitory activity of the sample was not changed at all. From this fact, it was found that Kexstatin is a thermo-stable substance. The pH values of aliquots of the above sample were adjusted to 2, 4, 6, 8 and 10 and these aliquots were left at room temperature overnight. Then, each pH value was re-adjusted to 7 and the inhibitory activity of each aliquot was determined. The results are shown in FIG. 2. As seen from this Figure, the activity was not changed at pH 6–8. Thus, it was found that Kexstatin is stable at pH 6–8.

EXAMPLE 3

Purification of Kexstatin Produced by Q268 Strain

Q268 strain was cultured in Waksman medium at 30° C. for 48 hr under aeration and cells were removed by centrifugation. The resulting culture fluid was treated at 100° C. for 5 min to thereby obtain 615 ml of the culture fluid. Since the Kex2 proteinase-inhibiting substance in the culture remains inside of a dialysis bag, the substance was presumed to be a polymer, probably, a protein. To the 615 ml culture fluid mentioned above, ammonium sulfate was added to give 80% (w/v) saturation and allowed to stand at 4° C. overnight. The precipitate was collected by centrifugation and dissolved in buffer A (20 mM Tris-HCl, pH 7.5). To the resulting solution, sufficiently cooled acetone was added. Then, the fractions precipitated with 50–60% (w/v) acetone were collected by centrifugation and dissolved in buffer A. The acetone-precipitated fractions were subjected to gel-filtration using a Sephadex G75 column (2.5×90 cm, Pharmacia) to collect those fractions exhibiting Kex2 proteinase-inhibiting activity. To 12 ml of the active fraction, 0.1 ml of 2% deoxycholic acid was added and allowed to stand at room temperature for 15 min. Then, 7.92 ml of 24% trichloroacetic acid was added thereto and allowed to stand for 30 min. The precipitated fraction was collected by centrifugation. The precipitate was washed with acetone, dried and then dissolved in 6 ml of buffer A. After the pH of the resulting solution was adjusted to 5.0 with 10% acetic acid, the solution was subjected to reversed phase column (Pro-RPC) chromatography (equipment: Pharmacia) of FPLC system using concentration gradients of acetonitrile solution containing 0.1% trifluoroacetic acid. Active fractions were recovered, freeze-dried and then dissolved in buffer A and stored at −20° C. From 615 ml of the culture fluid, 1.4 mg of the final, purified Kexstatin was obtained.

Figure 3:
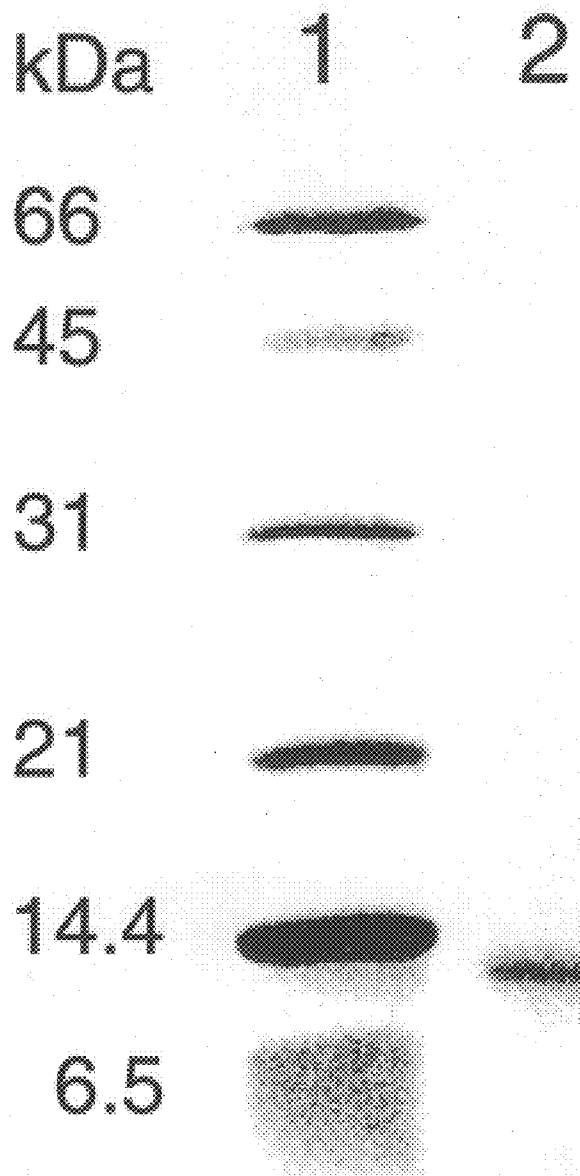
FIG. 3 is a photograph showing the SDS-polyacrylamide gel electrophoresis of Kexstatin.

FIG. 3 shows the results of SDS-polyacrylamide gel electrophoresis of the purified Kexstatin, which was electrophoretically homogeneous. Its molecular weight was calculated from comparison with the migration of the molecular weight marker and found to be 13,500. However, the molecular weight calculated from the entire amino acid sequence for Kexstatin (SEQ ID NO:10) is 11,787. Further, the molecular weight of the Kexstatin purified from culture fluid of *P. pastoris* transformed with a Kexstatin expression vector was recognized to be 11,500 (see FIG. 9). Thus, the molecular weight of Kexstatin has been decided to be 11,500.

EXAMPLE 4

Examination of Various Properties of Kexstatin

The inhibitory activity of Kexstatin against various proteinases was examined by the casein Folin method (Reimerdes, E. H. & Klostermeyer, H., (1976) Methods Enzymol., 45: 26–28; Lowry, O. H. et al., (1951) J. Biol. Chem., 193: 265–275). Briefly, casein was added to subtilisin, trypsin, chymotrypsin and thermolysin as a substrate, and the amount of acid-soluble peptides when Kexstatin was added and that amount when Kexstatin was not added were determined by Folin method. The inhibition ratios against individual enzymes are shown in Table 2 below.

TABLE 2

| Enzyme | Inhibition Ratio (%) |
| --- | --- |
| Subtilisin | 87 |
| Trypsin | 2.4 |
| Chymotrypsin | −19 |
| Thermolysin | −5.5 |

As Table 2 shows, Kexstatin inhibited subtilisin but did not inhibit other enzymes.

In order to examine the inhibitory activity of Kexstatin more accurately, the inhibitory activity against various proteinases was determined again. With respect to subtilisin, trypsin and chymotrypsin, the inhibitory activity was determined by a method using a synthetic fluorescent substrate. Briefly, each proteinase was incubated with a specific fluorescent substrate and the fluorescence intensity was measured employing an excitation wave length of 385 nm and a fluorescence wave length of 465 nm. With respect to thermolysin and pepsin, the inhibitory activity was determined by the casein Folin method in the same manner as described above. Inhibition ratios when individual enzymes were added to 0.5 μg of Kexstatin in an amount of 1/10 in molar ratio are shown in Table 3 below.

TABLE 3

| Enzyme | Substrate | Inhibition Ratio (%) |
| --- | --- | --- |
| Subtilisin | Suc—Ala—Ala—Pro—Phe—MCA | 99.5 |
| Trypsin | Bz—Arg—MCA | 49.2 |
| Chymotrypsin | Suc—Ala—Ala—Pro—Phe—MCA | 0 |
| Thermolysin | Casein | 8.0 |
| Pepsin | Casein | 0 |

As Table 3 shows, Kexstatin inhibited subtilisin and trypsin but did not inhibit other proteinases. The inhibition against trypsin is contradictory to the results described above. However, since the method using synthetic fluorescent substrates is superior to the casein Folin method in accuracy, the results of the latter measurement was taken and it was judged that Kexstatin has inhibitory activity against trypsin.

From the results described above, Kexstatin inhibits not only Kex2 proteinase family enzymes but also subtilisin and trypsin which are also serine proteinases. However, Kexstatin does not inhibit chymotrypsin (a serine proteinase) nor thermolysin and pepsin belonging to other type of proteinase. On the other hand, SSI which is a proteinaceous inhibitor against subtilisin inhibits subtilisin specifically and does not inhibit Kex2 proteinase, trypsin, chymotrypsin, thermolysin nor pepsin.

Figure 4:
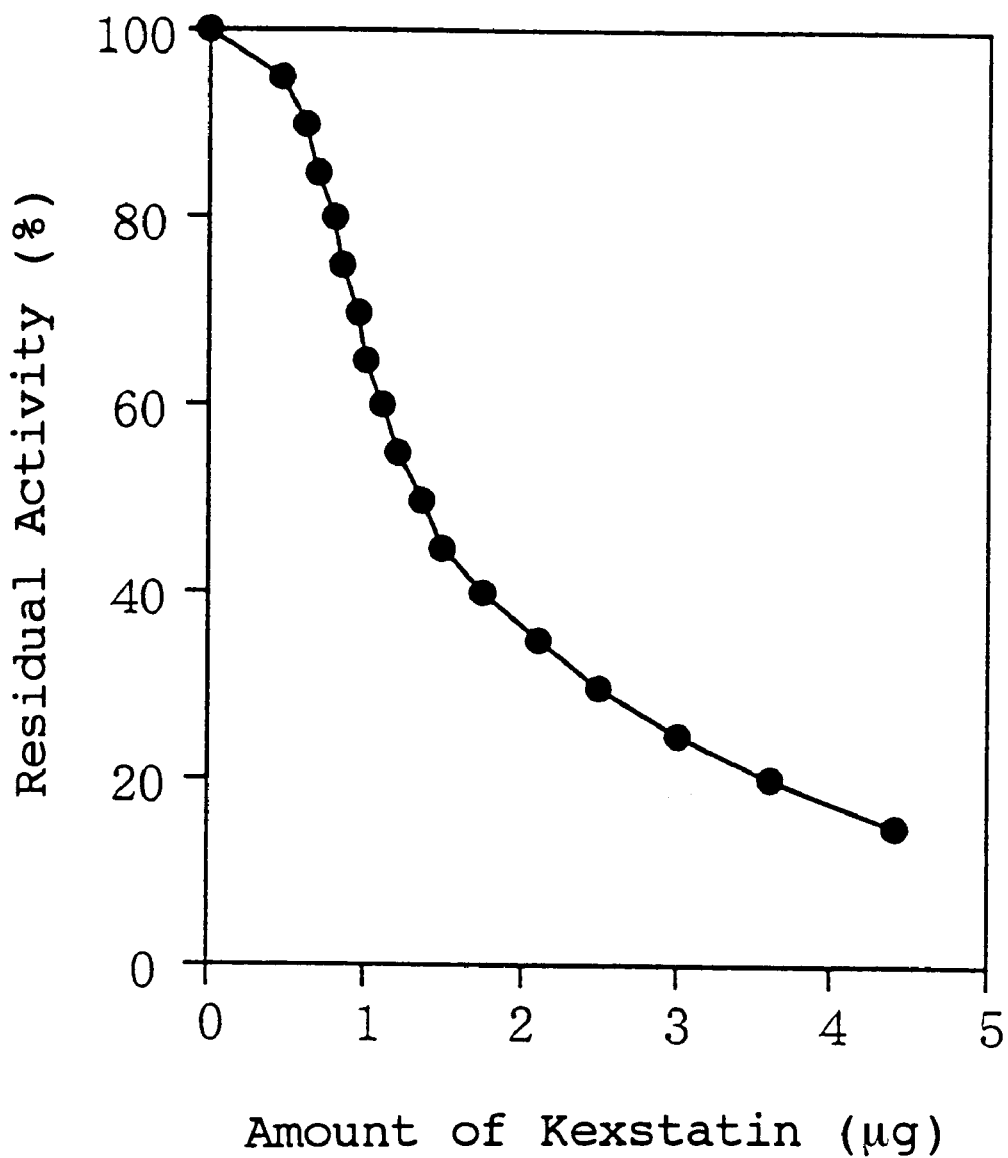
FIG. 4 is a graph showing the relationship between Kexstatin concentration and its inhibitory activity.
Figure 5:
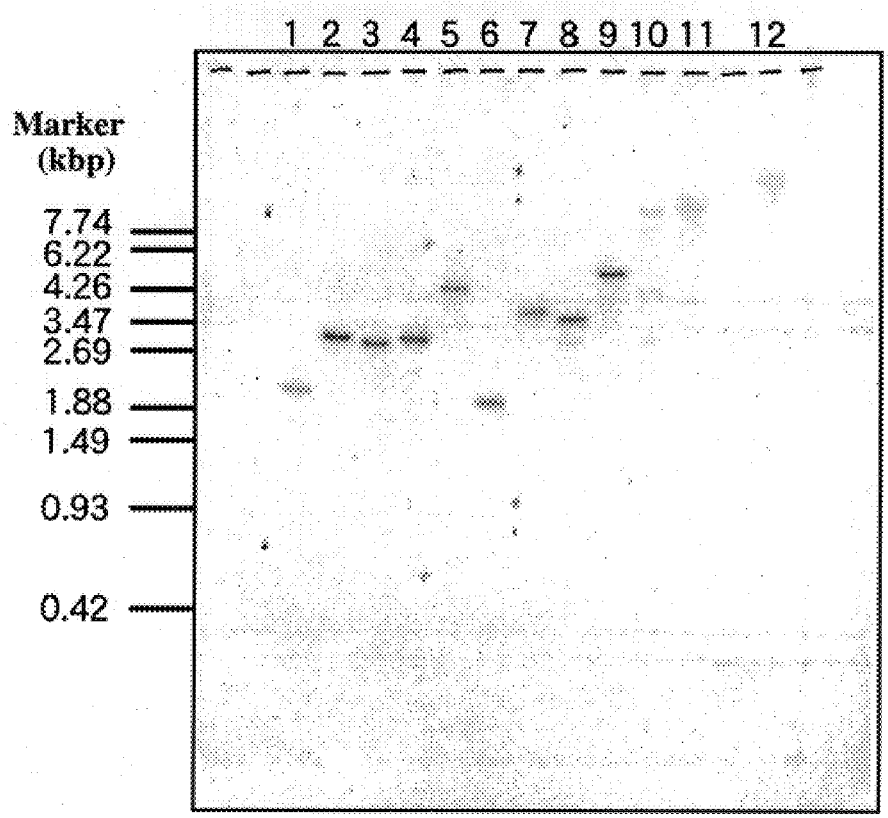
FIG. 5 is an autoradiograph showing the results of Southern hybridization of *Streptomyces platensis* genomic DNA.

The inhibitory activity of various concentrations of Kexstatin against Kex2 proteinase was examined by the method described in Example 1 (FIG. 4). The results show a typical pattern of antagonistic inhibition. The amount of Kexstatin which inhibits the activity of 1 µg of Kex2 proteinase by 50% (IC50) is calculated to be 1.4 µg. Considering the molecular weights of both substances, Kexstatin can be said an extremely strong inhibitor like SSI described above.

EXAMPLE 5

Determination of the Amino Acid Sequences for the Amino Terminal of Kexstatin and Trypsin-Digested Peptides Purified Kexstatin was electrophoresed on SDS-polyacrylamide gel (15%) and transferred to a PVDF (polyvinylidene difluoride) membrane. After the membrane was stained with Coomassie Brilliant Blue R250, the portion corresponding to Kexstatin was cut out and the sequence of its amino terminal was determined directly with an automated peptide sequencer (Perkin Elmer/Applied Biosystems 476A). The amino acid sequence for the 19 residues from the amino terminal was determined as follows.

Gly-Leu-Tyr-Ala-Pro-Thr-Glu-Leu-Val-Leu-Thr-Val-Gly-Gln-Gly-Glu-Ser-Arg-Ala-

Kexstatin (100 mg) was incubated in a solution containing 1 mg of trypsin and 0.1 M Tris-HCl buffer (pH 8.0) at 37° C. for 3 hr and then fractionated by high performance liquid chromatography (Gilson). The column used was Aquapore Butyl (Brownlee, 2.1 mm×220 mm) and was eluted by acetonitrile linear gradients in 0.1% trifluoroacetic acid. The absorbances at 220 nm and 280 nm were measured. Each of the peaks at 220 nm (TP1–TP5) were recovered, concentrated and dried. Then, the amino acid sequence for each peak was determined with an automated peptide sequencer (Perkin Elmer/Applied Biosystems 492). TP2 was subjected to chromatography again after reducing pyridylethylation and fractionated into TP2a and TP2b. TP5 was a double chain peptide and its amino acid sequence could not be determined.

The thus obtained amino acid sequences for individual peptide fragments are shown below.
TP1; Ala-Thr-Ala-Thr-Val-Gln-Arg
TP2a; Gly-Ser-His-Pro-Asn-Pro-Leu-Gly-Ala-Cys-Thr-Gln-Leu-Arg
TP2b; Ala-Val-Thr-Leu-Ser-Cys-Met-Pro-Gly-Ala-Arg
TP3; Gly-Leu-Tyr-Ala-Pro-Thr-Glu-Leu-Val-Leu-Thr-Val-Gly-Gln-Gly-Glu-Ser-Arg
TP4; Glu-Trp-Asn-Pro-Leu-Val-Val-Thr-Ala-Asp-Gly-Val-Trp-Gln-Gly-Lys-Arg When these sequences are compared with sequences stored in data bases, they exhibit a high similarity to amino acid sequences for proteinaceous proteinase inhibitors in the SSI family such as SSI (FIG. 8). Accordingly, it has been found that Kexstatin is a proteinase inhibitor belonging to the SSI family.

EXAMPLE 6

Cloning of Kexstatin Gene
1) Amplification of a DNA Fragment of Interest by PCR

Based on the amino acid sequence for peptide TP3 described in Example 5, the following sequence:

5'-ATTACGC(C/G)CC(C/G)AC(C/G)GA(A/G)CT-3' was synthesized as a sense primer, and based on the amino acid sequence for peptide TP4 described in Example 5, the following sequence:

5'- ATGCCCTGCCA(C/G)AC(C/G)CC(C/G)T-3' was synthesized as an antisense primer. A PCR was performed using these primers and the genomic DNA of Q268 strain as a template. First, the PCR solution was heated at 94° C. for 2 min. Thereafter, reaction was performed 30 cycles, each cycle consisting of:

Denaturation: 94° C., 1 min;

Annealing: 50° C., 1.5 min; and

Primer Extension: 72° C., 1.5 min.

Finally, the PCR solution was heated at 72° C. for 7 min. A PCR product of about 250 bp was subjected to DNA sequence analysis directly. As a result, it was found that the DNA sequence of this PCR product comprised nucleotide sequences corresponding to the amino acid sequences for peptides TP3 and TP4 described in Example 5, respectively. Thus, it was confirmed that this PCR product is a DNA fragment containing a portion of Kexstatin gene.

The PCR product was cloned and the plasmids were recovered. The entire nucleotide sequence of the inserted DNA fragment and the partial amino acid sequence of Kexstatin deduced therefrom were determined. The nucleotide sequence is shown in SEQ ID NO:7 and the amino acid sequence is shown in SEQ ID NO:8. The nucleotide sequence for 249 base pairs was determined and the amino acid sequence for 83 residues was elucidated.
2) Southern Hybridization Analysis of Genomic DNA Genomic DNA was isolated from cells of *Streptomyces platensis* Q268 strain. This isolation was performed in accordance with the method of Cryer et al. (Cryer, E. R. et al., (1975) Meth. Cell. Biol., 12: 39–44). The genomic DNA of *Streptomyces platensis* Q268 strain was digested with various restriction enzymes and separated by 1% agarose gel electrophoresis. The separated DNA was transferred from the gel to a nylon membrane (Amersham) and fixed.

The PCR product described above was labeled with $^{32}$P using a Nick Translation Kit (Amersham). The labeled PCR product was added to a solution containing 5×SSC, 1% SDS and 1× Denhardt solution to prepare a hybridization solution. This hybridization solution was added to the nylon membrane on which the DNA was fixed and then the membrane was sealed in a plastic bag. The nylon membrane sealed in the bag was incubated at 65° C. for 16 hr. Thereafter, the membrane was taken out of the bag and washed with a solution containing 2×SSC and 1% SDS at room temperature.

Subsequently, the nylon membrane was incubated in a solution containing 0.2×SSC and 0.1% SDS at 65° C. for 30 min. Then, the solution was replaced with fresh solution and the membrane was further incubated at 65° C. for 30 min. After the membrane was washed with 2×SSC and dried, autoradiography was performed. A BamHI-SalI fragment of about 2 kb was found as the minimum DNA fragment hybridizing with the 250 bp probe described above.
3) Cloning of Kexstatin Gene by Colony Hybridization The genomic DNA of *Streptomyces platensis* Q268 strain was completely digested with the restriction enzymes BamHI and SalI and fractionated by 1% agarose gel electrophoresis. A portion of the agarose gel around 2 kb was cut out and a DNA fragment was recovered with a DNA cell (Daiichi Kagaku). The recovered DNA fragment was inserted in pUC119 digested with BamHI and SalI. Then, *E. coli* JM109 strain was transformed with this plasmid to construct the genomic library of *Streptomyces platensis* Q268 strain. This library was screened by colony hybridization using the above-mentioned 250 bp DNA fragment as a probe to thereby obtain a positive clone. The hybridization conditions were the same as in the Southern hybridization described above.

Figure 6:
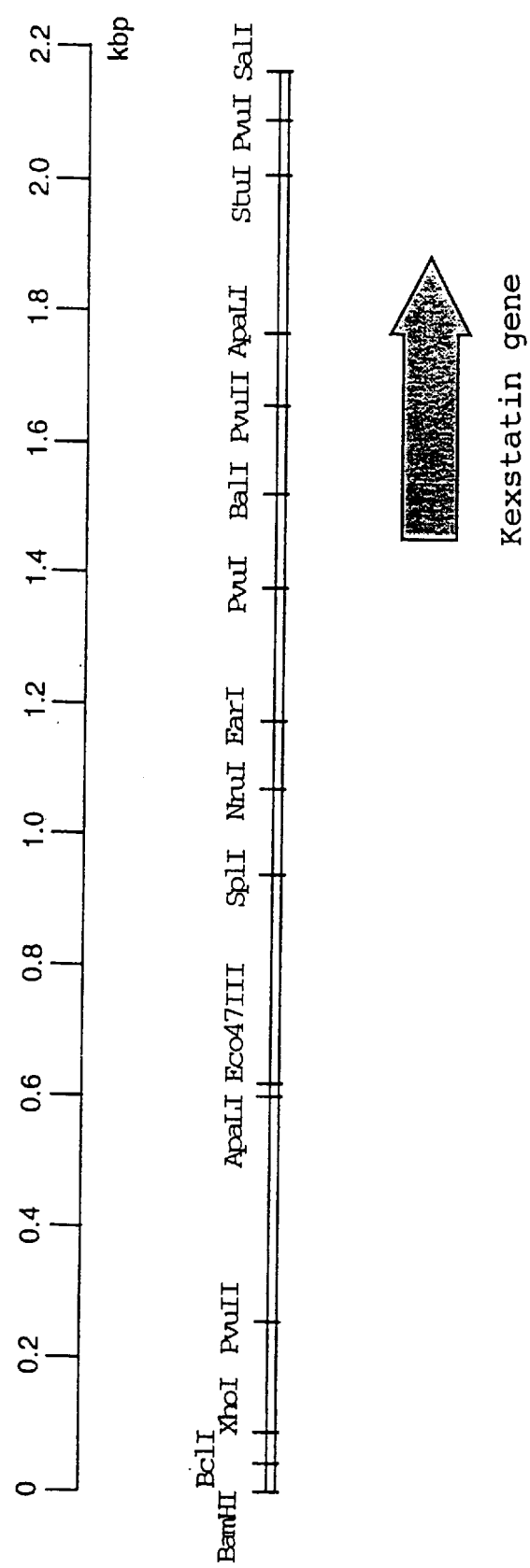
FIG. 6 shows a restriction map of a 2 kb DNA fragment containing a Kexstatin gene.

Plasmids were recovered from the positive clone and the nucleotide sequence for the 2186 base pairs of the inserted, about 2 kb DNA fragment was determined. In this nucleotide sequence, 9 open reading frames (ORFs) were found. In the amino acid sequence encoded by one ORF starting from the ATG at position 1477 and ending at position 1911, sequences identical with the partial amino acid sequences of Kexstatin shown in SEQ ID NOS: 2–6 were found. The entire nucleotide sequence for the 2186 base pairs is shown in SEQ ID NO: 9 and the amino acid sequence for Kexstatin deduced from the nucleotide sequence is shown in SEQ ID NO: 10. The restriction map of this inserted DNA fragment is shown in FIG. 6.

The partial nucleotide sequence from position 1201 to position 2186 and the amino acid sequence for the Kexstatin precursor encoded by this DNA fragment are shown in FIG. 7. The Kexstatin precursor consists of 145 amino acids. The amino terminal 35 residues function as a signal peptide (the underlined portion in the amino acid sequence in FIG. 7) and a mature-type Kexstatin consisting of 110 amino acids is secreted. Fifteen bases upstream of the initiation codon, there is found a ribosome binding sequence (the boxed portion in FIG. 7). A palindrome sequence (the underlined portion in the nucleotide sequence in FIG. 7) involved in the termination of transcription is found downstream of the termination codon.

When the amino acid sequence for Kexstatin is compared with amino acid sequences stored in data bases, it exhibits a high similarity to amino acid sequences for proteinaceous proteinase inhibitors in the SSI (*Streptomyces subtilisin* inhibitor) family (FIG. 8). Accordingly, it has been found that Kexstatin is a proteinase inhibitor belonging to the SSI family. Further, the amino acid residue at the reactive site of Kexstatin is lysine which is also found at the reactive site of other SSI family inhibitors.

EXAMPLE 7

Expression of Kexstatin in Methylotropic Yeast

In order to express the Kexstatin gene obtained, the methylotropic yeast *Pichia pastoris* was used which is greatly effective in efficient expression, in particular, secretory expression of a heterogeneous protein. Expression vectors for *P. pastoris* and the host methylotropic yeast are commercially available as a kit from Invitrogen Corporation, San Diego City, USA. The restriction maps, nucleotide sequences, etc. of the expression vectors and the genetic type, etc. of the host strains *P. pastoris* are described in detail in the manual attached to the kit. The transformation of *P. pastoris,* the selection of the transformant, the cultivation of the transformant, and so forth were performed according to the methods described in the manual.

In order to insert Kexstatin gene into an expression vector for *P. pastoris,* an XhoI site and a BamHI site were created on the amino terminal side and the carboxyl terminal side of the mature-type Kexstatin, respectively. Briefly, the following sequence:

5'-CTCGAGGCCTCTACGCCCCGAC-3' was synthesized as a sense primer and the following sequence:

5'-GGATCCTCAGAAGTTGAAGACCG-3' was synthesized as an antisense primer. With these two primers, a PCR was performed using a DNA fragment containing Kexstatin gene as a template. The amplified DNA fragments were treated with XhoI and BamHI and then cloned. It was confirmed that the nucleotide sequence for the XhoI-BamHI fragment was not different from the nucleotide sequence for Kexstatin gene. The XhoI-BamHI fragment encodes the amino acid sequence for the mature-type Kexstatin having addition of Arg at the amino terminal.

As the expression vector for *P. pastoris,* pHIL-S1 was used. When a gene of interest is inserted downstream of the signal sequence for acid phosphatase (PH01) in pHIL-S1, this plasmid is able to allow the expression of a fusion protein between the gene product of interest and the PH01 signal sequence, and the gene product of interest can be secreted by the function of the above signal sequence. Since the gene of the fusion protein is inserted between the promoter and the terminator of alcohol oxidase gene, the expression of the gene can be induced by addition of methanol to the medium. pHIL-S1 has HIS4 gene which is necessary for the incorporation of an inserted gene into the chromosomal DNA of *P. pastoris* and for the selection of transformed yeast; a selection marker in *E. coli;* and a replication origin in *E. coli*. The XhoI-BamI fragment described above which codes for the mature-type Kexstatin was inserted into the XhoI-BamHI site in pHIL-S1 to thereby prepare a recombinant plasmid. This recombinant plasmid was treated with SalI to make it linear. Then, *P. pastoris* GS115 strain (his4) was transformed with the plasmid. The transformant yeast selected based on His+ was cultured in BMMY medium containing 0.5% methanol at 30° C. for 5 days. The culture fluid was analyzed by SDS-polyacrylamide gel electrophoresis (FIG. 9).

Figure 9:
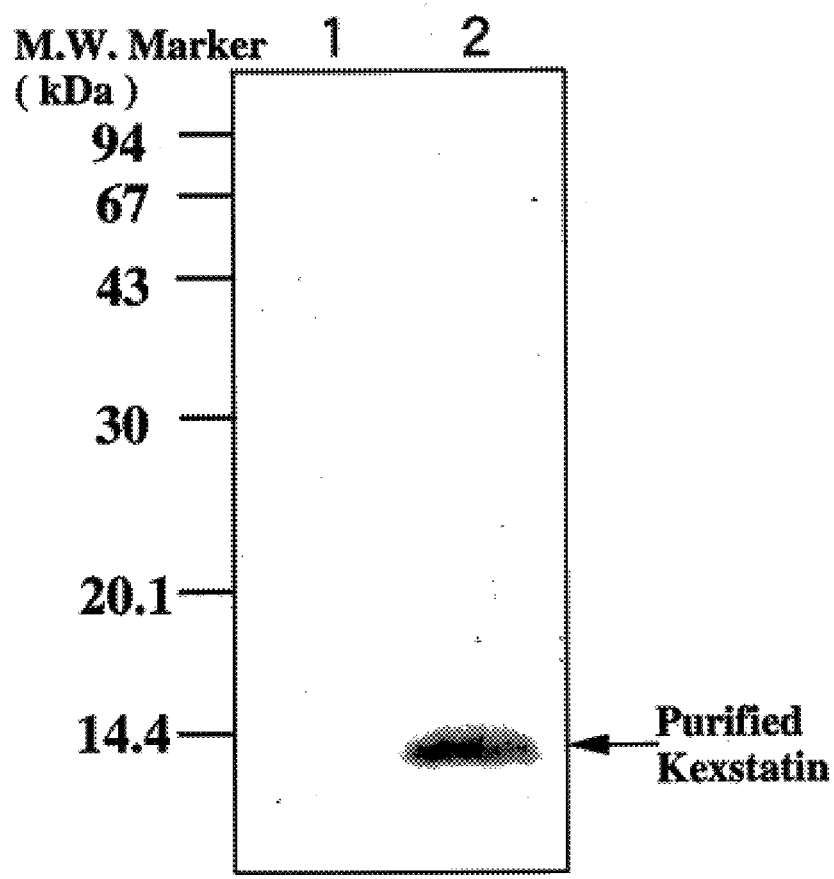
FIG. 9 is a photograph showing the SDS-polyacrylamide gel electrophoresis of a culture fluid of a methanol yeast expressing Kexstatin.

While a band of 11,500 daltons in molecular weight showing almost the same mobility as that of purified Kexstatin is recognized in the culture fluid (25 ml) of *P. pastoris* transformed with the Kexstatin expression vector (lane 2 in FIG. 9), this band is not recognized in the culture fluid of *P. pastoris* transformed with the vector pHIL-S1 (lane 1 in FIG. 9). Also, Kex2 proteinase inhibitory activity was only recognized in the culture fluid of *P. pastoris* transformed with the Kexstatin expression vector.

EFFECT OF THE INVENTION

The present invention provides a novel proteinase inhibitor useful as medicines, pesticides and the like, and the gene of the proteinase inhibitor.

What is claimed is:

1. A proteinase inhibitor having inhibitory activity against Kex2 proteinase family enzymes, comprising the amino acid sequences shown in SEQ ID NOS: 2 to 6 and conservatively modified variants thereof.

2. A proteinase inhibitor having inhibitory activity against Kex2 proteinase family enzymes and having a molecular weight of about 11,500, said proteinase inhibitor having an amino acid sequence comprising the amino acid sequence shown in SEQ ID NO: 10 or conservatively modified variants thereof.

3. An isolated protein comprising an amino acid sequence as set forth in SEQ ID NO: 8.

4. An isolated protein comprising an amino acid sequence as set forth in SEQ ID NO: 10.

5. The isolated protein according to claim 4, which is a proteinase inhibitor having a molecular weight of about 11.5 kDa as determined by SD S-PAGE, and having inhibitory activity against Kex 2 family proteinases.

6. The proteinase inhibitor according to claim 2, wherein the proteinase inhibitor also inhibits subtilisin and trypsin.

7. The proteinase inhibitor according to claim 6, wherein the proteinase inhibitor does not inhibit chymotrypsin, thermolysin, or pepsin.

8. The proteinase inhibitor according to claim 7, wherein the proteinase inhibitor is thermostable.

9. The proteinase inhibitor according to claim 8, wherein the proteinase inhibitor is stable from about pH 6 to about pH 8.

10. The proteinase inhibitor according to claim 9, wherein the proteinase inhibitor has an $IC_{50}$ of about 1.4 micrograms.

11. A proteinase inhibitor having an amino acid sequence shown in SEQ ID NO: 10 or, conservatively modified variants thereof, and having the following physicochemical properties (a) to (g):

(a) maintains inhibitory activity against Kex2 proteinase family enzymes;

(b) inhibits subtilisin and trypsin;

(c) does not inhibit chymotrypsin, thermolysin, or pepsin;

(d) has a molecular weight of about 11,500;

(e) is thermostable;

(f) stable from about pH 6 to about pH 8;

(g) has an $IC_{50}$ of about 1.4 micrograms.

* * * * *